US007850706B2

United States Patent
Regner et al.

(10) Patent No.: US 7,850,706 B2
(45) Date of Patent: Dec. 14, 2010

(54) PANCREATIC-ENTERIC FISTULARY CATHETERIZATION SYSTEM

(75) Inventors: Justin L. Regner, North Little Rock, AR (US); Michael J. Edwards, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 687 days.

(21) Appl. No.: 11/890,925

(22) Filed: Aug. 8, 2007

(65) Prior Publication Data

US 2009/0043319 A1    Feb. 12, 2009

(51) Int. Cl.
A61B 17/08    (2006.01)
A61M 5/00    (2006.01)

(52) U.S. Cl. .......................................... 606/153; 604/8

(58) Field of Classification Search ................. 606/153, 606/154, 213; 604/8, 9, 264, 523, 507, 508, 604/317, 327
See application file for complete search history.

(56) References Cited

U.S. PATENT DOCUMENTS

| | | | | | |
|---|---|---|---|---|---|
| 2,638,901 | A | * | 5/1953 | Sugarbaker | 606/153 |
| 4,055,186 | A | * | 10/1977 | Leveen | 606/153 |
| 4,154,241 | A | * | 5/1979 | Rudie | 606/153 |
| 4,294,255 | A | * | 10/1981 | Geroc | 606/153 |
| 4,392,855 | A | | 7/1983 | Oreopoulos et al. | |
| 4,467,804 | A | * | 8/1984 | Hardy et al. | 606/154 |
| 4,553,960 | A | | 11/1985 | Lazarus et al. | |
| 4,705,039 | A | * | 11/1987 | Sakaguchi et al. | 606/154 |
| 4,719,917 | A | * | 1/1988 | Barrows et al. | 606/220 |
| 4,753,236 | A | * | 6/1988 | Healey | 606/153 |
| 4,766,898 | A | * | 8/1988 | Hardy et al. | 606/154 |

(Continued)

FOREIGN PATENT DOCUMENTS

WO    WO 95/02367    1/1996

(Continued)

OTHER PUBLICATIONS

Office Action, Jul. 31, 2008, U.S. Appl. No. 11/229,970, filed Sep. 19, 2005, First Named Inventor—Justin Regner.

(Continued)

*Primary Examiner*—Julian W Woo
*Assistant Examiner*—Christopher L Templeton
(74) *Attorney, Agent, or Firm*—Ray F. Cox, Jr.

(57) ABSTRACT

A catheterization system for forming dual sutureless anastomoses using two catheters connectable to one another. Once the fistula is healed, a dissolvable connection allows the catheters to separate one from the other and the separated pieces are extruded through normal bowel action. The two catheters may be connected in various ways. In one embodiment, a separate guide member may be used to pull a dissolvable suture through the first catheter. The suture is then attached to the second catheter and the suture may be used to pull the second catheter into contact with the first catheter so that the two catheters are closely connected by the suture. When the suture dissolves, the two catheters separate. In another embodiment, the first catheter has a section formed of a dissolvable mesh. The two catheters may be connected together by any of various types of connections. After a period of time, the mesh dissolves and allows the joined catheters to separate into two pieces.

14 Claims, 14 Drawing Sheets

U.S. PATENT DOCUMENTS

| | | | | |
|---|---|---|---|---|
| 4,930,502 | A * | 6/1990 | Chen | 606/150 |
| 5,123,908 | A * | 6/1992 | Chen | 606/153 |
| 5,259,847 | A | 11/1993 | Trambert | |
| 5,297,547 | A | 3/1994 | Brain | |
| 5,411,508 | A * | 5/1995 | Bessler et al. | 606/153 |
| 5,458,570 | A * | 10/1995 | May, Jr. | 604/500 |
| 5,527,324 | A | 6/1996 | Krantz et al. | |
| 5,549,122 | A | 8/1996 | Detweilwer | |
| 5,599,291 | A * | 2/1997 | Balbierz et al. | 604/8 |
| 5,890,316 | A * | 4/1999 | Rodgers et al. | 43/43.16 |
| 6,187,008 | B1 * | 2/2001 | Hamman | 606/318 |
| 6,290,728 | B1 | 9/2001 | Phelps et al. | |
| 6,565,581 | B1 * | 5/2003 | Spence et al. | 606/153 |
| 6,666,873 | B1 * | 12/2003 | Cassell | 606/153 |
| 6,699,280 | B2 * | 3/2004 | Camrud et al. | 623/1.16 |
| 2001/0001825 | A1 | 5/2001 | Snow et al. | |
| 2002/0123698 | A1 * | 9/2002 | Garibotto et al. | 600/585 |
| 2002/0143329 | A1 * | 10/2002 | Serhan et al. | 606/61 |
| 2004/0087986 | A1 * | 5/2004 | Ott | 606/153 |
| 2004/0193092 | A1 | 9/2004 | Deal | |
| 2004/0249470 | A1 | 12/2004 | Whitmore, III | |
| 2005/0049577 | A1 | 3/2005 | Snell et al. | |
| 2005/0049626 | A1 | 3/2005 | Burgard | |
| 2005/0137614 | A1 * | 6/2005 | Porter et al. | 606/153 |
| 2005/0222671 | A1 * | 10/2005 | Schaeffer et al. | 623/1.15 |
| 2005/0283111 | A1 * | 12/2005 | Maurice | 604/43 |
| 2006/0004393 | A1 * | 1/2006 | Amarant | 606/153 |
| 2006/0015144 | A1 * | 1/2006 | Burbank et al. | 606/219 |
| 2007/0031508 | A1 * | 2/2007 | Armstrong et al. | 424/572 |
| 2007/0066982 | A1 | 3/2007 | Regner et al. | |
| 2007/0142850 | A1 * | 6/2007 | Fowler | 606/153 |
| 2007/0213810 | A1 * | 9/2007 | Newhauser et al. | 623/1.16 |

FOREIGN PATENT DOCUMENTS

| | | |
|---|---|---|
| WO | WO 2007/035262 A2 | 3/2007 |
| WO | WO 2007/035262 A3 | 3/2007 |
| WO | WO2009/020505 A1 | 2/2009 |

OTHER PUBLICATIONS

Advisory Action, U.S. Appl. No. 11/229,970, filed Sep. 19, 2005, First Named Inventor-Regner, J.), Mailed Feb. 26, 2009.

International Preliminary Report on Patentability, International Application No. PCT/US2008/008380, Feb. 18, 2010.

Cameron, J., et al., Long Term Transhepatic Intubation for Hilar Hepatic Duct Structures, Ann. Sur., vol. 193, No. 5, May 1976, pp. 488-495.

Wexler, M., et al., Jejunal Mucosal Graft, The American Journal of Surgery, vol. 129, Feb. 1975, pp. 204-211.

International Search Report and Written Opinion of International Searching Authority, PCT/US06/34753, Apr. 6, 2007, 7 pages.

Office Action, USPTO, in U.S. Appl. No. 11/229,970, filed Sep. 19, 2005, First Named Inventor-Regner, J., Aug. 11, 2008.

International Search Report and Written Opinion of International Searching Authority, PCT/US08/08380, Oct. 29, 2008.

Office Action, U.S. Appl. No. 11/229,970, filed Sep. 19, 2005, First Named Inventor-Justin, R.), Mailing Date Dec. 19, 2008, 10 pages.

* cited by examiner

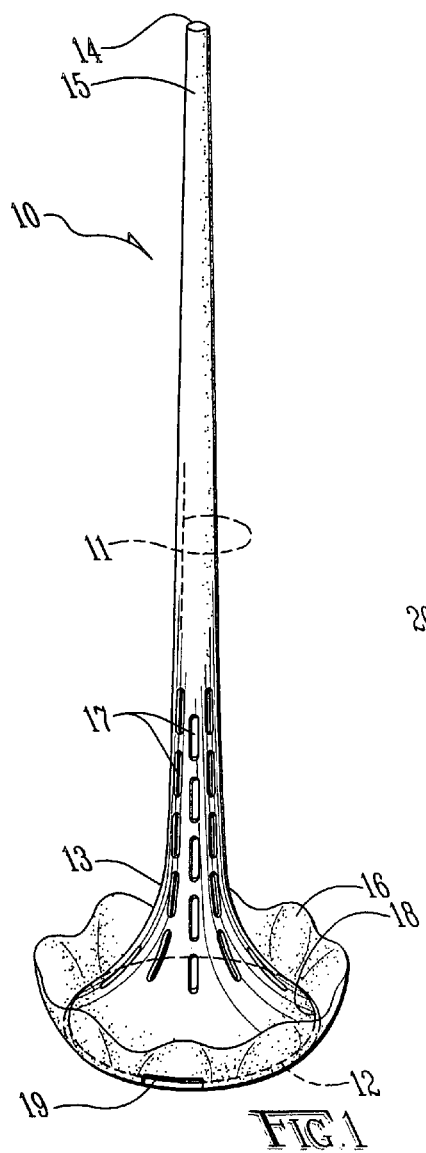
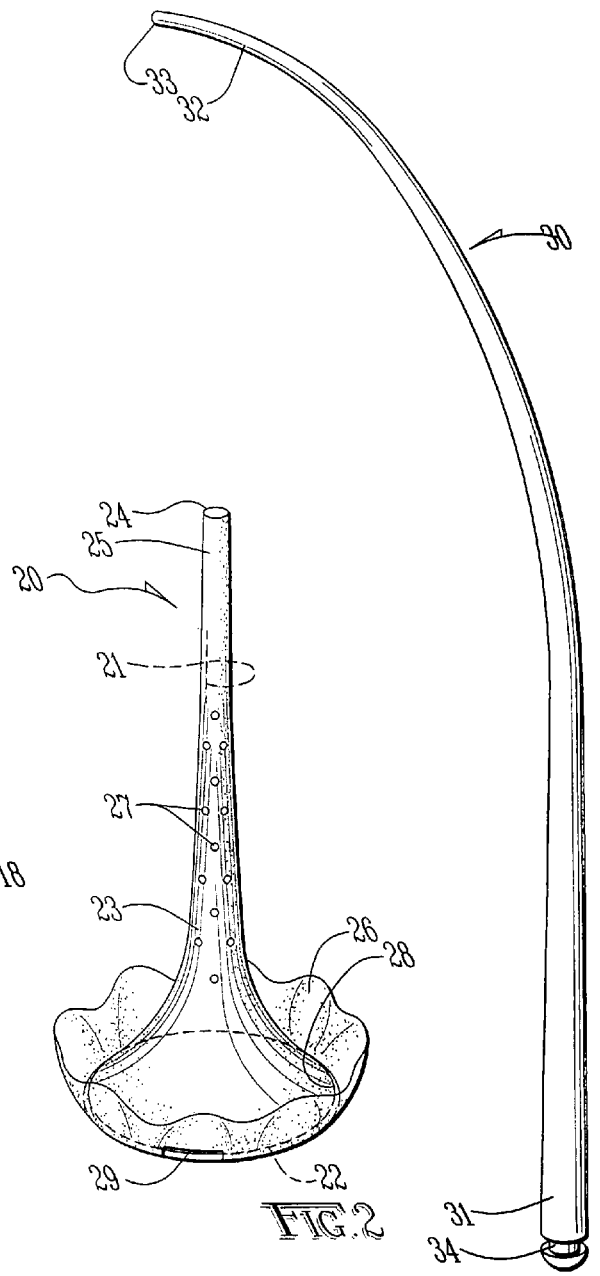
FIG. 1
FIG. 2
FIG. 3

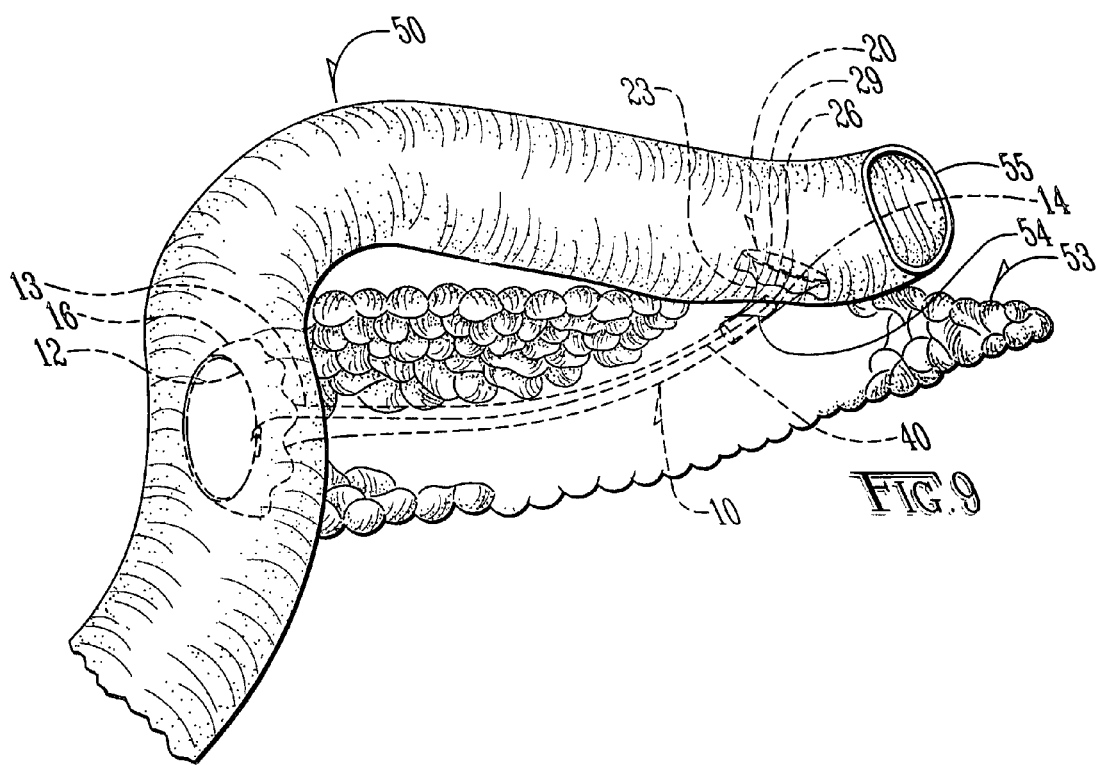

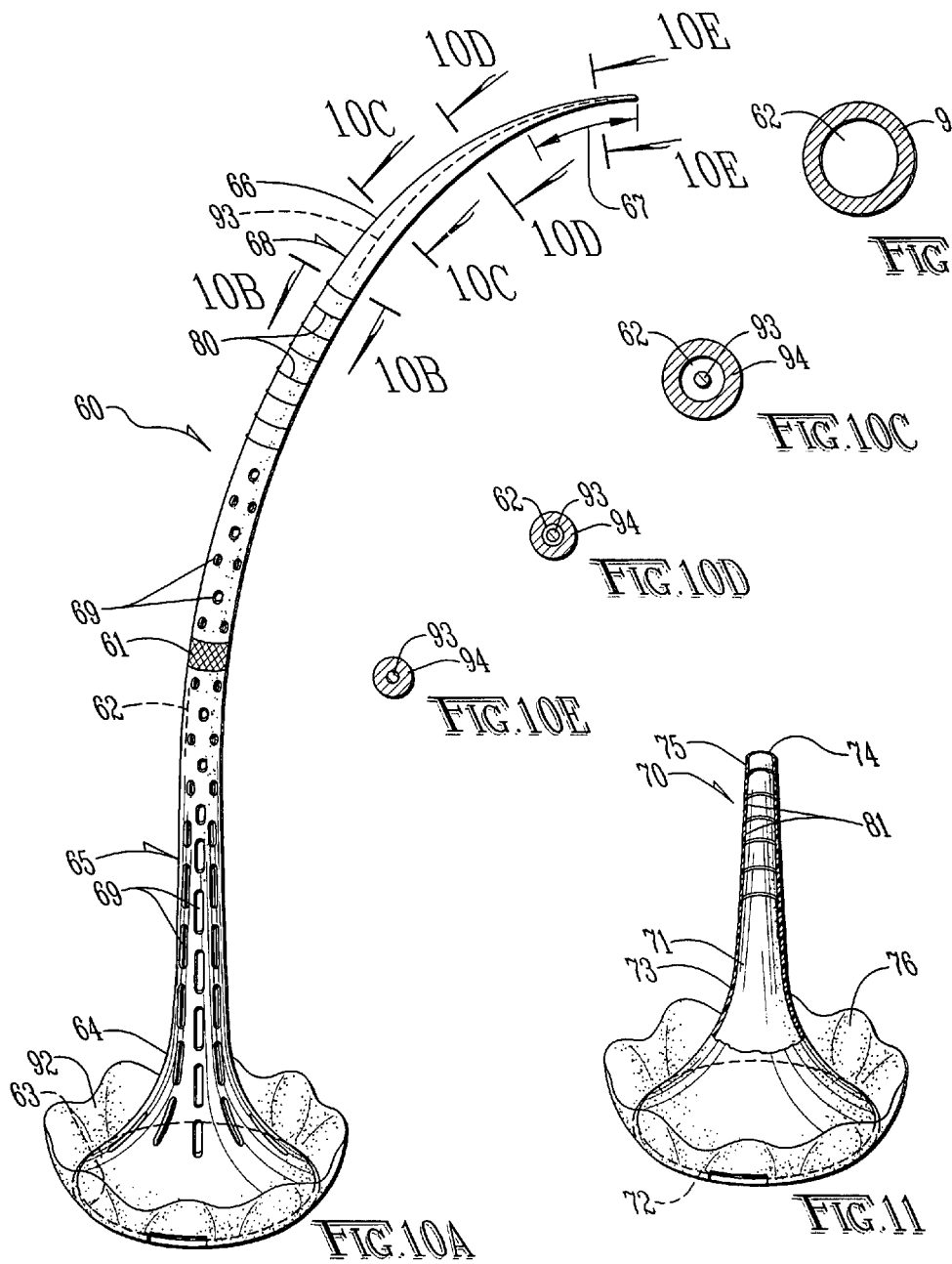

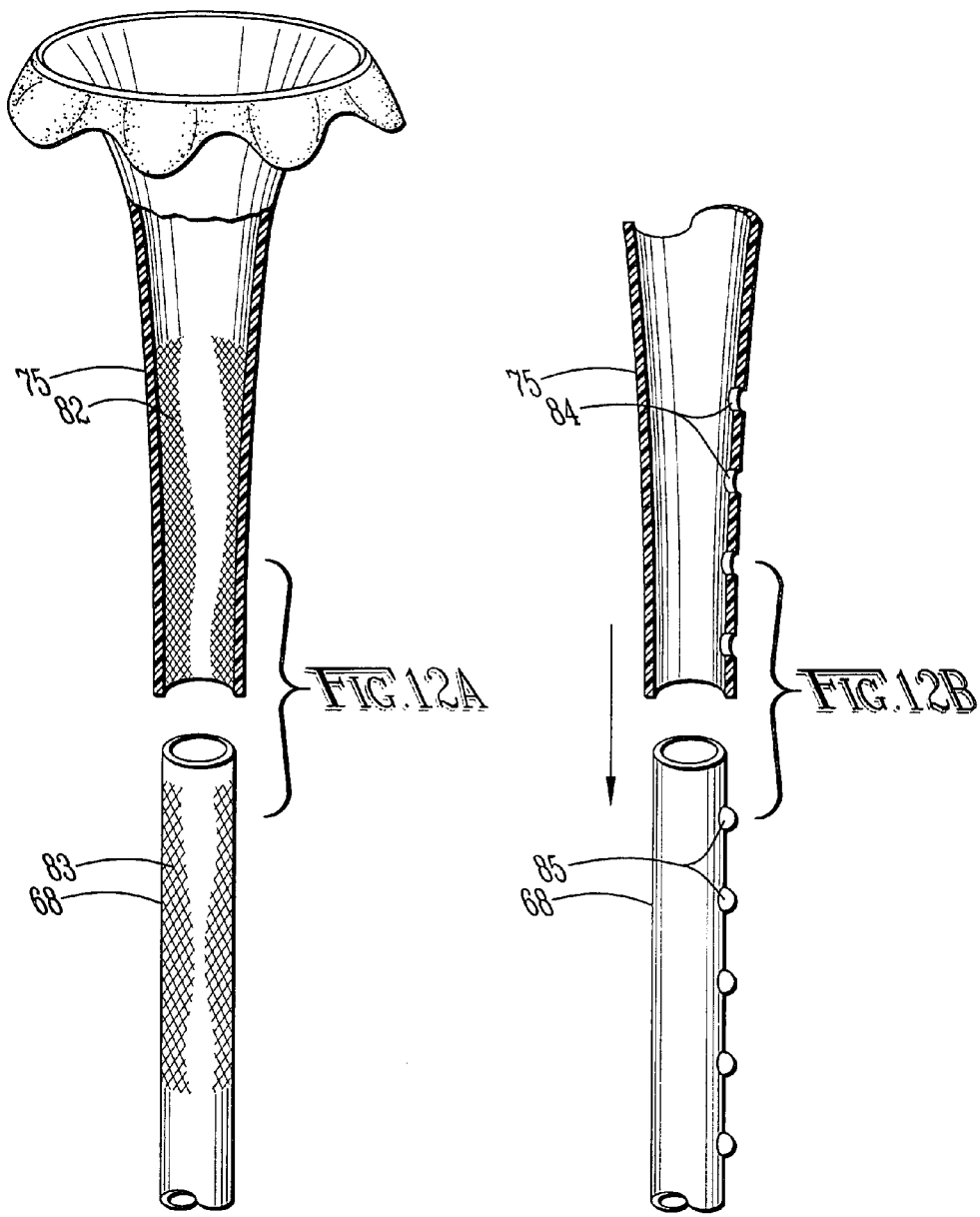

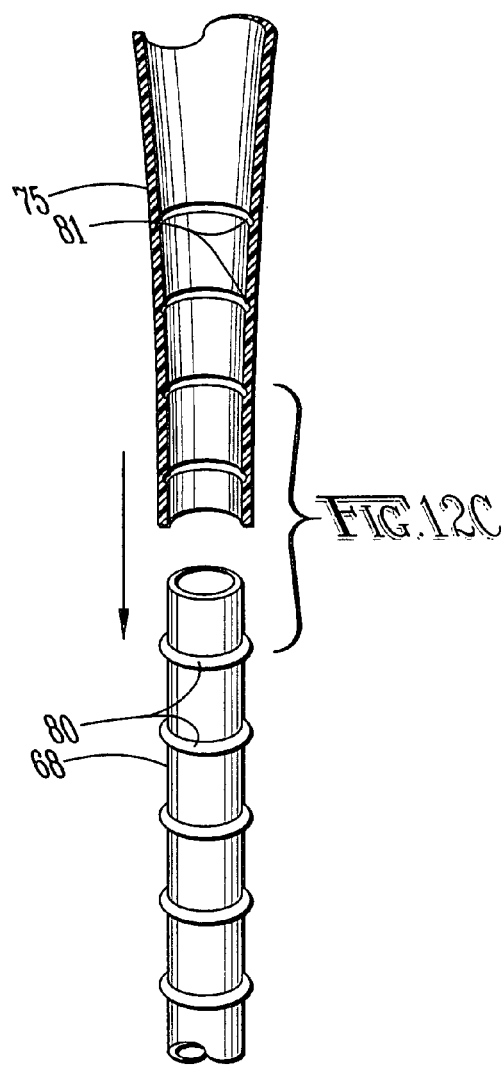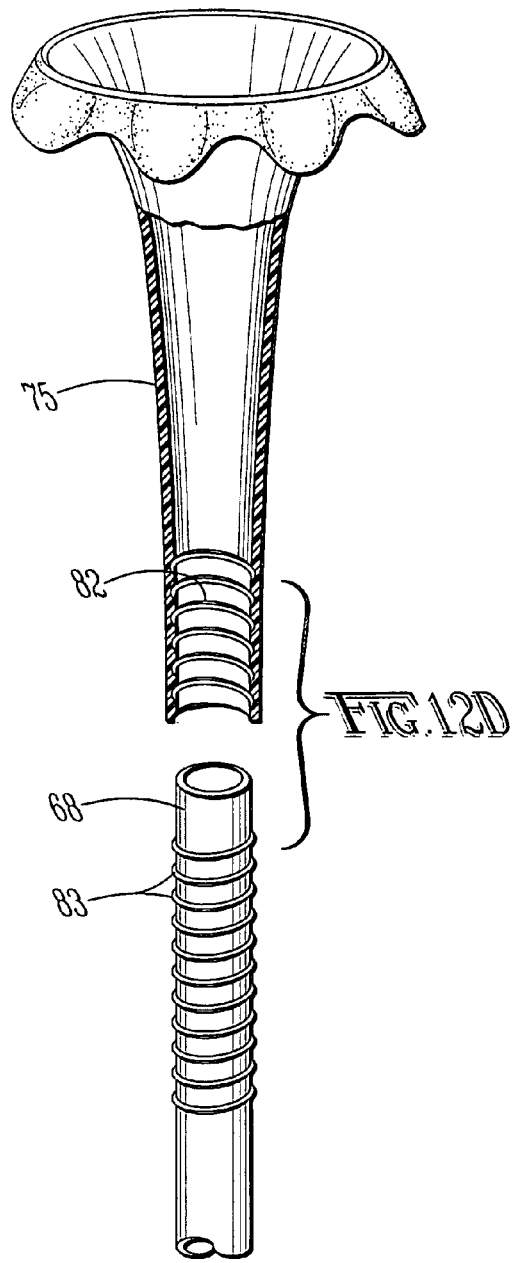

PANCREATIC-ENTERIC FISTULARY CATHETERIZATION SYSTEM

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates to a catheterization system to create dual sutureless anastomoses between two normally separate spaces in the human or animal body, and in particular for such a catheterization system for creating an anastomosis between the pancreatic duct and the small bowel lumen.

2. Brief Description of the Related Art

There are various medical reasons for creating an anastomosis, i.e., an opening or connection between two vessels or between two normally separate spaces within a human or animal body. See, for example, U.S. patent application Ser. No. 11/229,970, filed Sep. 19, 2005 and published on Mar. 22, 2007 as Pub. No. US 2007/0066982 A1, the disclosure of which is incorporated herein by reference. For example, it may be desirable to create a passage (a fistula) to allow the drainage of fluids from an organ whose normal outlet is blocked or to create a new passage in any organ where the typical anatomy must be resected for disease pathology. One such condition involves the blockage of the pancreatic ducts which requires the creation of a communication between the pancreas and the small intestine. It is standard operating technique to create a sutured anastomosis over an existing tube/stent involving the pancreatic duct and small bowel. This tube is not sutured in place and passes in the enteric tract within a few days.

BRIEF SUMMARY OF THE INVENTION

The present invention is a catheterization system to create patent epithelialized connections between the epithelium of the pancreatic duct and the epithelium of the small bowel. The present invention does not require the use of traditional suture or staples and provides a seal between the two organs with decreased risk of leaks or disruptions. Once the fistula has healed, the device breaks into two separate pieces to be extruded from the patient's body with normal bowel function.

The catheterization system comprises two flanged catheters: one catheter is for a fistula through the pancreatic duct and the other attaches through the parenchyma, the functional element of the pancreas. In order to create a pancreatic-enteric sutureless anastomosis, a Roux limb or loop of small intestine is created and an enterotomy is made in the Roux limb. The flange of the first catheter grips the mucosa of the Roux limb through the enterotomy. The first catheter is introduced to the pancreatic duct by means of a guide member, such as a wire, that may be separate from the catheter or may be incorporated into the catheter as an integral unit. The guide member and catheter penetrate the pancreatic parenchyma and exit through the pancreatic serosal surface. The flange of the second catheter grips the mucosa of the Roux limb through a second enterotomy and then connects to the first catheter. When the two catheters are snuggly joined, two anastomoses are formed—one between the mucosa at the first enterotomy and the pancreatic duct and the other between the mucosa of the second enterotomy and the artificial exit from the parenchyma.

The two catheters may be connected in various ways. In one embodiment, a dissolvable suture is attached to the separate guide member and the first catheter. The separate guide member is inserted through the first catheter. The first catheter and guide member may be used as a unit as described above to enter the pancreatic duct, penetrate the pancreas and exit through the parenchyma. The guide member is then removed from the first catheter and the dissolvable suture is pulled through the first catheter. The suture is then attached to the second catheter and the suture may be used to pull the second catheter into contact with the first catheter so that the two catheters are closely connected by the suture. When the suture dissolves, the two catheters separate and are extruded by normal bowel action.

In another embodiment, one of the first or second catheters has a section formed of a dissolvable mesh made of a material such as vicryl or monocryl and an integral guide member. The two catheters may be connected together by any of various types of snap-fit or other connections. After a period of time, the dissolvable mesh section dissolves and allows the joined catheters to separate into two pieces. Once the two pieces separate, they are extruded with normal bowel movements.

Both catheters include an attachment flange that decreases the risk of necrosis to epithelial attachments, thereby decreasing the risk of stricture, stenosis or leaks.

This device allows more efficient operating maneuvers for the surgeon, thus decreasing operative times and operative complications.

The features of the present invention may be used with other devices, such as gastrostomy and jejunostomy tubes. The process of the present invention may also be applied to laparoscopic procedures, thus facilitating conversion of difficult open pancreatic procedures to more facile minimally invasive procedures. Potentially the present invention may be applied to all intestinal anastomoses in both open and closed procedures.

These and other features, objects and advantages of the present invention will become better understood from a consideration of the following detailed description of the preferred embodiments and appended claims in conjunction with the drawings as described following:

BRIEF DESCRIPTION OF THE SEVERAL VIEWS OF THE DRAWINGS

FIG. 1 is a perspective view of an embodiment of a first catheter.

FIG. 2 is a perspective view of an embodiment of a second catheter.

FIG. 3 is a perspective view of an embodiment of a guide member.

FIG. 9 is a perspective view illustrating the second catheter secured to the first catheter.

FIG. 10A is a perspective view of an alternative embodiment of the first catheter. FIGS. 10B-E are cross sections of the guide section and guide wire along the lines 10B-10B through 10E-10E, respectively, of FIG. 10A.

FIG. 11 is a perspective view of an alternative embodiment of the second catheter.

FIG. 12A is a partial perspective view of the first and second catheters illustrating a frictional means of attachment of the first and second catheters.

FIG. 12B is a partial perspective view of the first and second catheters illustrating a elastic protuberance and hole means of attachment of the first and second catheters.

FIG. 12C is a partial perspective view of the first and second catheters illustrating a rib and complementary recess means of attachment of the first and second catheters.

FIG. 12D is a partial perspective view of the first and second catheters illustrating a screw means of attachment of the first and second catheters.

DETAILED DESCRIPTION OF THE INVENTION

Figure 4:
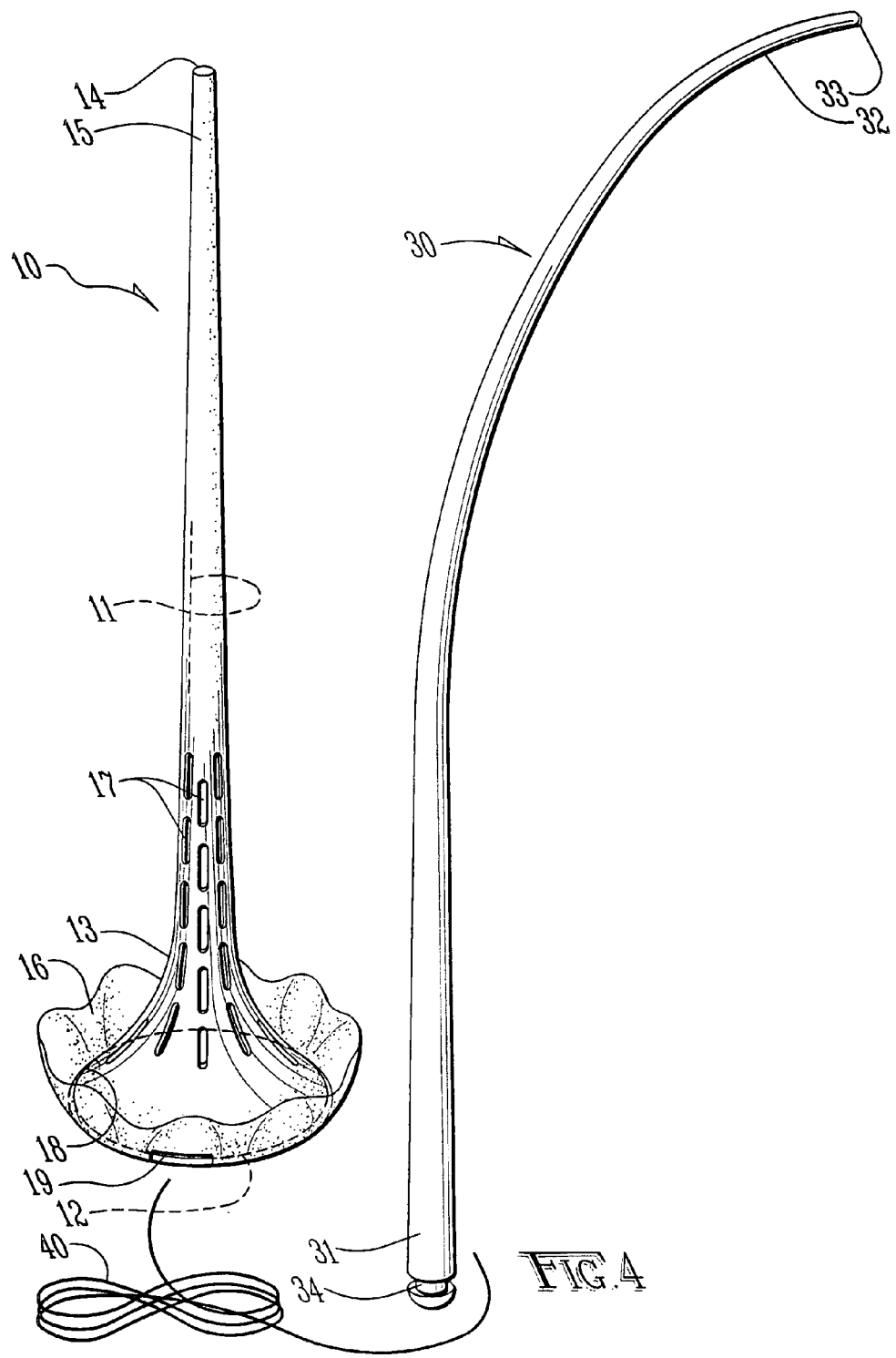
FIG. 4 is a perspective view of the first catheter of FIG. 1 attached to the guide member of FIG. 3 by a dissolvable suture.

The catheterization system of the present invention comprises two flanged catheters: one catheter is for a fistula through the pancreatic duct and the other attaches through the parenchyma, the functional element of the pancreas. The catheters described herein are desirably made of any of various elastic materials, such as latex, vinyl chloride or Silastic ® silicone rubber. Silastic ® silicone rubber will not promote an inflammatory reaction at the site where the guide member exits the surface of the pancreas. However, an inflammatory reaction may be desirable to better seal the exit site. For the purpose of promoting an inflammatory reaction, latex is the preferred material.

An embodiment of the present invention is described following with reference to FIGS. 1-9.

An embodiment of a first catheter 10 is shown in FIG. 1. The first catheter 10 is an elongated, generally tubular elastic structure having a hollow interior 11 communicating with a first opening 12 at a first end 13 and a second opening 14 at a second end 15. The first catheter 10 may be provided with a flare toward the first end 13. A flange 16 is disposed around the first opening 12. The flange may, for example, be of the type disclosed in U.S. patent application Ser. No. 11/229,970, cited above, which is an everted rim of the first end 13 and may be corrugated to minimize necrosis of the epithelium. The first catheter 10 may also incorporate fenestrations 17 disposed along at least a portion of the length of the first catheter 10 and communicating with the hollow interior 11. The first catheter 10 also incorporates means for attaching a dissolvable suture. Preferably, the means for attaching a dissolvable suture comprises a ring 18, preferably of metal, disposed around the opening 12 and a gap 19 through the flange 16 and the first end 13 to allow a suture to be passed through the gap 19 and around the ring 18.

An embodiment of a second catheter 20 is shown in FIG. 2. The second catheter 20 is an elongated, generally tubular structure that may be shorter than the first catheter 10. The second catheter 20 has a hollow interior 21 communicating with a first opening 22 at a first end 23 and a second opening 24 at a second end 25. Preferably, the second end 25 of the second catheter 20 is sized so as to fit snugly within the second end 15 of the first catheter 10. The second catheter 20 may be provided with a flare toward the first end 23. A flange 26 is disposed around the first opening 22. As with the first catheter 10, the flange may be of the type disclosed in U.S. patent application Ser. No. 11/229,970. The second catheter 20 may also incorporate fenestrations 27 disposed along at least a portion of the length of the second catheter 20 and communicating with the hollow interior 21. The second catheter 20 also incorporates means for attaching a dissolvable suture. Preferably, the means for attaching a dissolvable suture comprises a ring 28, preferably of metal, disposed around the opening 22 and a gap 29 through the flange 26 and the first end 23 to allow a suture to be passed through the gap 29 and around the ring 28.

With reference to FIG. 3, a separate guide member, preferably a guide wire 30, is provided to be used in conjunction with the first catheter 10. The guide wire 30 is generally tapered from a first end 31 to a second end 32. The guide wire 30 may be substantially straight along its length or may be hooked or curved as shown in FIG. 3 to facilitate its passage into the pancreatic duct. The second end 32 terminates in a penetrating point 33 which is preferably rounded or blunt for penetrating through the parenchyma. The first end 31 provided means for attachment of a dissolving suture. The means for attachment may be a circumferential recess 34 in the first end 31.

Figure 5:
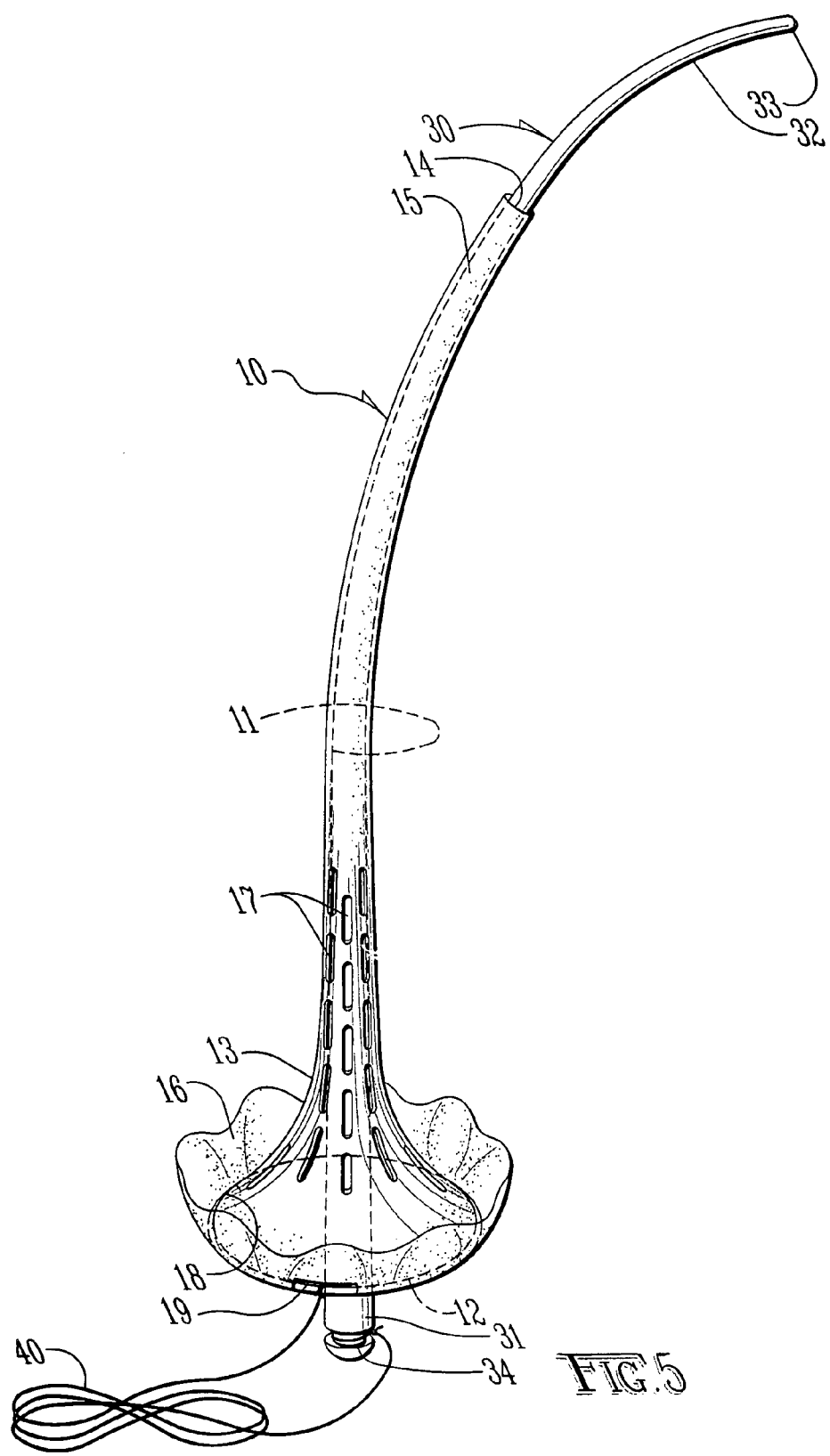
FIG. 5 is a perspective view of the guide member assembled to the first catheter.
Figure 6:
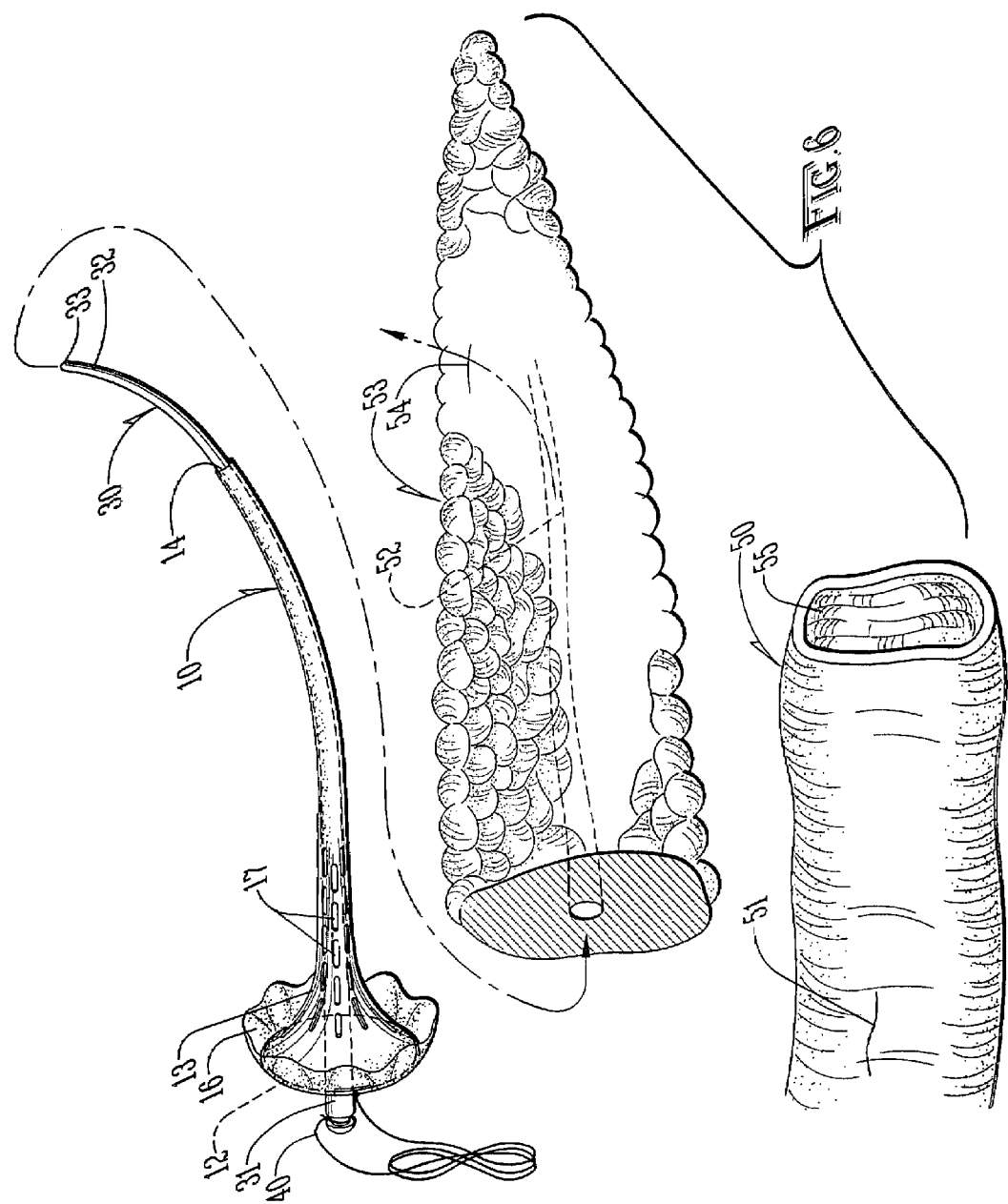
FIG. 6 is an exploded perspective view illustrating guiding the assembled first catheter and guide member into the pancreatic duct.

A length of dissolvable suture 40, such as 2-0 vicryl, is attached to the first catheter 10 and the guide wire 30 by tying one end of the suture 40 to the ring 18 as described above and tying the other end of the suture 40 to the circumferential recess 34 in the guide wire 30. Then, as shown in FIG. 5, the guide wire 30 is slipped into the first opening 12 and through the first catheter 10 until the second end 32 of the guide wire 30 protrudes from the second opening 14 of the first catheter 10. It is desirable that the second end 15 of the first catheter 10 be tapered for a smooth transition between the first catheter 10 and the guide wire 30 in order to minimize tissue damage and drag. Once the first catheter 10 and the guide wire 30 have been assembled together, they can be employed as a unit.

Figure 7:
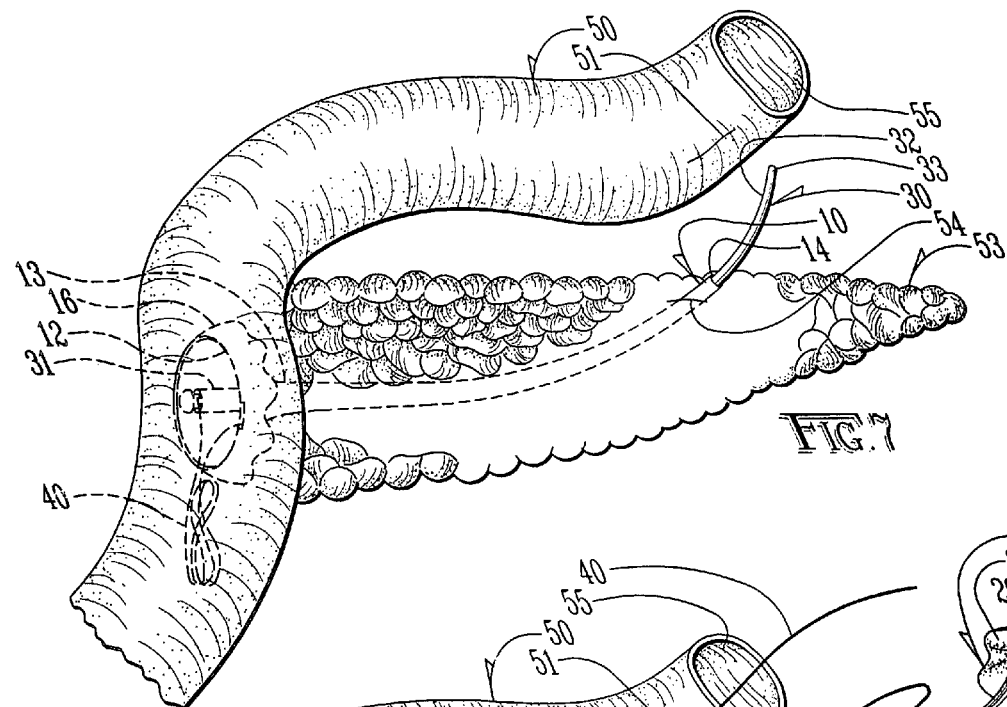
FIG. 7 is a perspective view illustrating securing the Roux limb to the pancreatic duct.

The following description is given for illustrative purposes with respect to a Roux limb of the small intestine. However, the present invention is not limited to use with a Roux limb. For example, a loop of jejunum could be used in the practice of the present invention. Similarly, the stomach and the Roux limb or jejunal limb could be used in combination. The present invention may also be used in a pancreatic pseudocyst with anastomosis to the stomach, Roux limb or jejunal loop. With respect to a Roux limb 50 as shown in FIGS. 6-9, in order to create a pancreatic-enteric sutureless anastomosis, the Roux limb 50 is created and an enterotomy 51 is made in the Roux limb 50. The assembled first catheter 10 and guide wire 30 are guided through the duct 52 of the pancreas 53. The guide wire 30 penetrates the pancreas 53 and exits the parenchyma at an exit opening 54. The flange 16 of the first catheter is inserted through the incision 51 where it is positioned to grip the mucosa of the Roux limb through the enterotomy 51. Alternatively, the assembled first catheter 10 and guide wire 30 may first be inserted through the open end 55 of the Roux limb 50 and out through the enterotomy 51 before being guided into the pancreatic duct 52. Also, as described below, a donut shaped member 90 may be employed to assist in placing the flange 16 within the enterotomy 51. In any of these approaches, the Roux limb 50 is thereby secured to the pancreas 53 by the flange 16 of the first catheter 10 as shown in FIG. 7.

Figure 8:
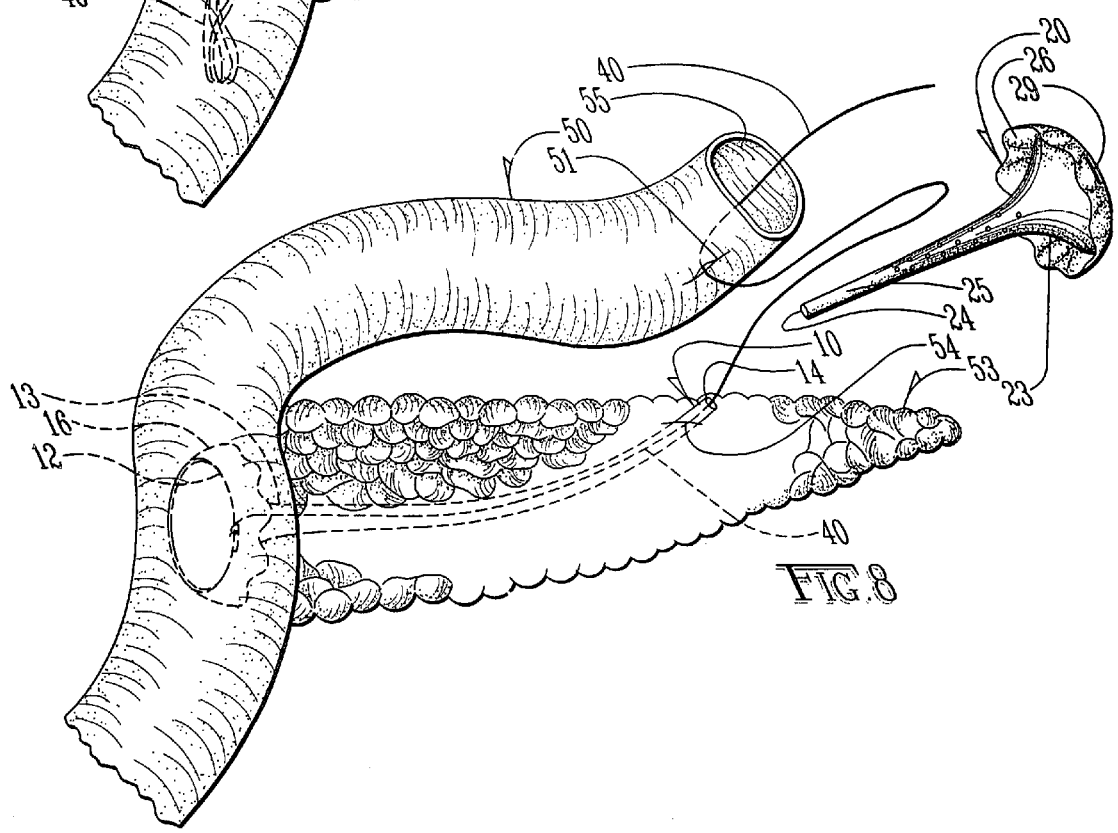
FIG. 8 is a perspective view illustrating the attachment of the second catheter to the first catheter.

The guide wire 30 is then pulled through the first catheter 10 dragging the suture 40 with it. As shown in FIG. 8, the guide wire 30 with the attached suture 40 is passed through a second incision 56 in the Roux limb and out the open end 55 of the Roux limb 50. The end of the suture 40 is then detached from the guide wire 30, passed through the hollow interior 21 of the second catheter 20. The second catheter 20 is passed into the open end 55 of the Roux limb 50 until the second end 25 of the second catheter 20 enters snuggly into the second end 15 of the first catheter. As shown in FIG. 9, the suture 40 is then attached to the ring 28 of the second catheter 20. The flange 16 of the first catheter 10 and the flange 26 of the second catheter 20 form two anastomoses—one between the mucosa at the first enterotomy 51 and the pancreatic duct 52 and the other between the mucosa of the second enterotomy 56 and the exit opening 54 from the parenchyma. After sufficient time for the anastomoses to heal, the suture 40 dissolves, the two catheters 10, 20 separate and are extruded by normal bowel action.

In another embodiment of the present invention as shown in FIGS. 10-13B, a first catheter 60 has a dissolvable section 61, which may be formed of a dissolvable mesh made of a material such as vicryl or monocryl, and an integral guide member such as guide wire 93. Although this embodiment is described with reference to the dissolvable mesh section 61 formed in the first catheter, the dissolvable mesh section 61 may alternatively be formed in the second catheter 70. The first catheter 60 is an elongated, generally tubular structure having a hollow interior 62 communicating with an opening 63 at a first end 64 and a guide section 66 at a second end 67. The first catheter 60 may be provided with a flare toward the first end 64. The first catheter comprises a first section 65 between the opening 63 and the dissolvable section 61 and a second section 68 between the dissolvable section 61 and a guide section 66. A flange 92 is disposed around the opening 63. The flange may, for example, be of the type disclosed in U.S. patent application Ser. No. 11/229,970, cited above, which is an everted rim of the first end 64 and may be corrugated to minimize necrosis of the epithelium. The first catheter 60 may incorporate fenestrations 69 disposed along at least a portion of the length of the first section 65 and/or the second section 68. The fenestrations 69 communicate with the hollow interior 62. The second section 68 also comprises means for attachment to the second catheter 70 as described more fully below.

The first catheter 60 may be substantially straight along its length or may be provided with a hook or curve in at least a portion of the second section 68 and/or the guide section 66. The entirety of the second section 68 is a continuation of the hollow interior 62 and in communication with the opening 63, while some or all of the guide section 66 may be a continuation of the hollow interior 62 with a guide wire 93, preferably metallic, disposed in the guide section 66. The disposition of the guide wire 93 in relation to the wall 94 of the guide section 66 is shown in FIGS. 10B-E, which are cross sections of the guide section 66.

An embodiment of a second catheter 70 is shown in FIG. 11. The second catheter 70 is an elongated, generally tubular structure that may be shorter than the first catheter 60. The second catheter 70 has a hollow interior 71 communicating with a first opening 72 at a first end 73 and a second opening 74 at a second end 75. The second catheter 70 may be provided with a flare toward the first end 73. A flange 76 is disposed around the first opening 72. As with the first catheter 60, the flange 76 may be of the type disclosed in U.S. patent application Ser. No. 11/229,970. The second catheter 70 may also incorporate fenestrations (not shown) disposed along at least a portion of the length of the second catheter 70 and communicating with the hollow interior 71. The second catheter 70 is provided with means for attachment to the means for attachment of the second section 68 of the first catheter 60.

Figures 13A, 13B:
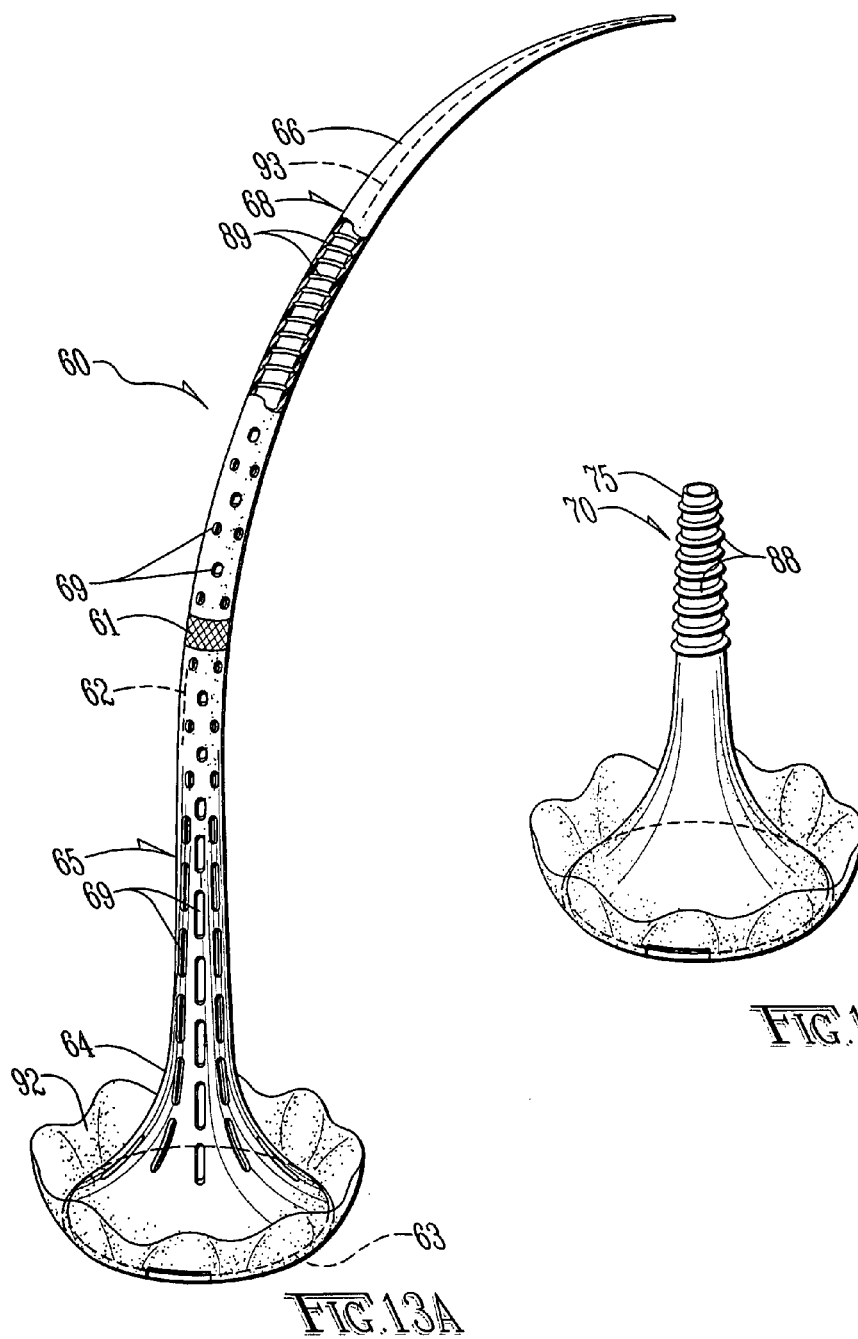
FIGS. 13A and 13B are perspective views of an alternative embodiment to that of FIG. 12C.

The means for connection of the two catheters 60, 70 may be any of various types of snap-fit or other connections. As shown in FIGS. 10, 11 and 12C, the first catheter 60 may be provided with a plurality of ribs 80 along at least a portion of the exterior surface of the second section 68. The second catheter 70 may be provided with a plurality of complementary recesses 81 on at least a portion of the interior surface of the second end 75. In this embodiment, after the guide section 66 of the first catheter 60 is removed as described below, the second end 75 of the second catheter 70 is sized to pass over the remaining portion of the second section 68 of the first catheter 60 and to elastically engage the plurality of ribs 80 with the plurality of complementary recesses 81. Alternatively, as shown in FIGS. 13A and 13B, the second catheter 70 may be provided with a plurality of ribs 88 on at least a portion of the exterior surface of the second end 75. The first catheter 60 may be provided with a plurality of complementary recesses 89 along at least a portion of the interior surface of the second section 68. In this alternative embodiment, after the guide section 66 of the first catheter 60 is removed as described below, the second end 75 of the second catheter 70 is sized to pass into the remaining portion of the second section 68 of the first catheter 60 and to elastically engage the plurality of ribs 88 with the plurality of complementary recesses 89.

Other means for connection are shown in FIGS. 12A, 12B and 12D. In FIG. 12A, at least a portion of the interior surface of the second end 75 of the second catheter 70 is provided with a frictional surface 82 for frictionally engaging a complementary frictional surface 83 on at least a portion of the exterior surface of the second section 68 of the first catheter 60. In FIG. 12B, at least a portion of the second end 75 of the second catheter 70 is provided with a plurality of openings 84 for elastically engaging a plurality of complementary elastic protuberances 85 on at least a portion of the exterior surface of the second section 68 of the first catheter 60. In FIG. 12D, at least a portion of the interior surface of the second end 75 of the second catheter 70 is provided with a set of screw threads 86 for threadedly engaging a complementary set of screw threads 87 on at least a portion of the exterior surface of the second section 68 of the first catheter 60. As with the alternative embodiment of FIGS. 13A and 13B, any of the other embodiments described above with respect to FIGS. 12A, 12B and 12D may be reversed so that the second end 75 of the second catheter 70 is sized to pass into the remaining portion of the second section 68 of the first catheter 60.

Figure 14:
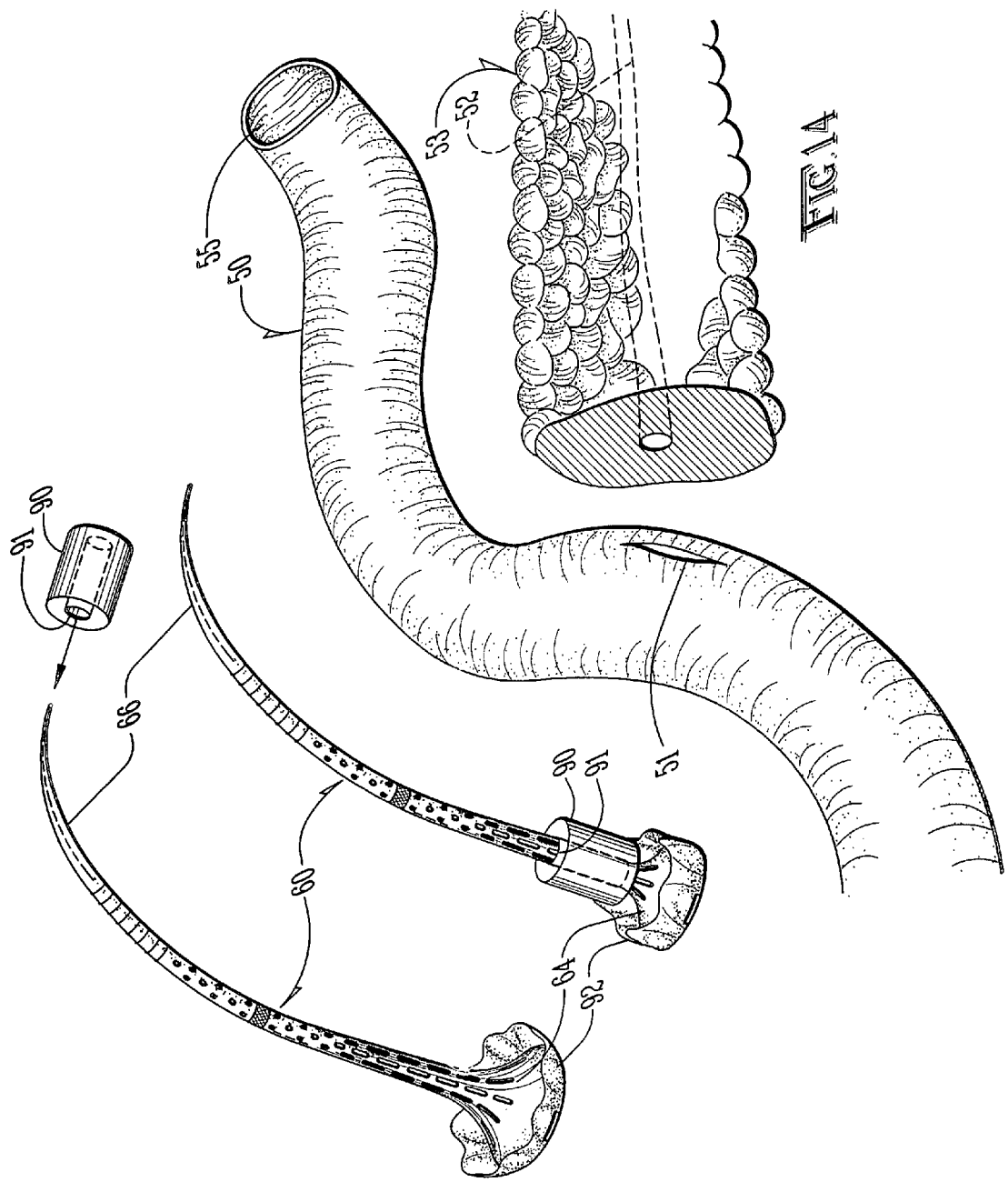
FIGS. 14-18 are perspective views showing the steps in one method of attachment of the catheters of the alternative embodiments of FIGS. 10A and 11.
Figure 15:
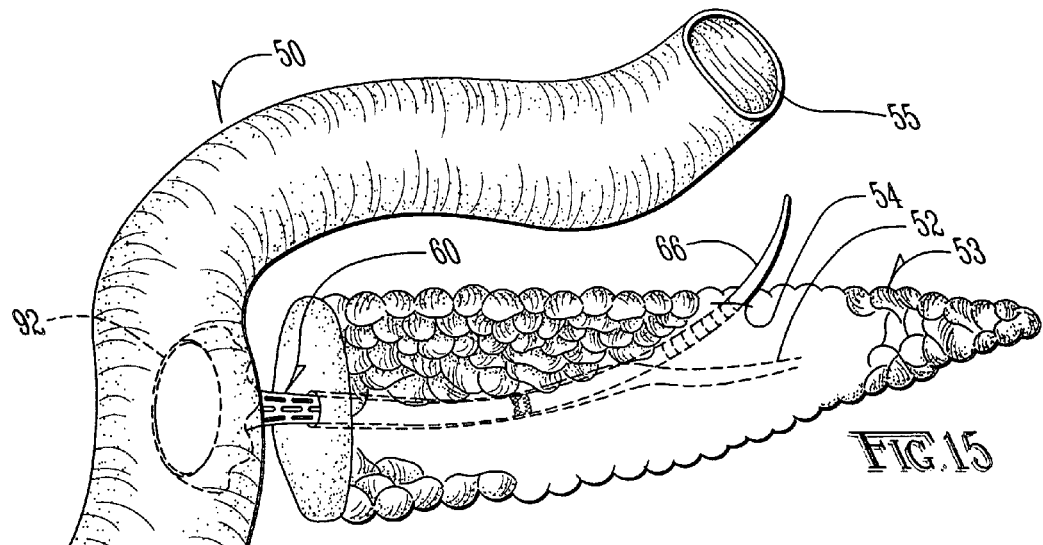

The following description is given with reference to FIGS. 14-20 illustrating the present invention with respect to a Roux limb. Other than the Roux limb, the present invention may be used in various alternative scenarios known to those of ordinary skill in the art since clinical practice depends on the surgeon's preference and the patient's anatomy. In order to create a pancreatic-enteric sutureless anastomosis with a Roux limb 50 and the embodiment of FIGS. 10-13B, the Roux limb 50 is created and an enterotomy 51 is made in the Roux limb 50. A donut-shaped member 90 with a bore 91 narrower than a diameter of the flared portion of the first end 64 is placed over the guide section 66 and passed down the first catheter 60 toward the flared portion in order to draw in and narrow the elastic flange 92 as shown in FIG. 14. A smaller enterotomy 51 is possible when using a narrowed flange 92. The narrowed flange 92 is inserted into the smaller enterotomy 51 and when the donut shaped member 90 is withdrawn, the flange 92 expands to its original shape inside the enterotomy 51 as shown in FIG. 15 where it is positioned to grip the mucosa of the Roux limb 50. The guide section 66 of the first catheter 60 is then guided through the duct 52 of the pancreas 53. The guide section 66 penetrates the pancreas 53 and exits the parenchyma at an exit opening 54. Alternatively, the first catheter 60 may first be inserted through the open end 55 of the Roux limb 50 and out through the enterotomy 51 before being guided into the pancreatic duct 52. In either case, the Roux limb 50 is thereby secured to the pancreas 53 by the flange 92 of the first catheter 60 as shown in FIG. 15.

Figure 16:
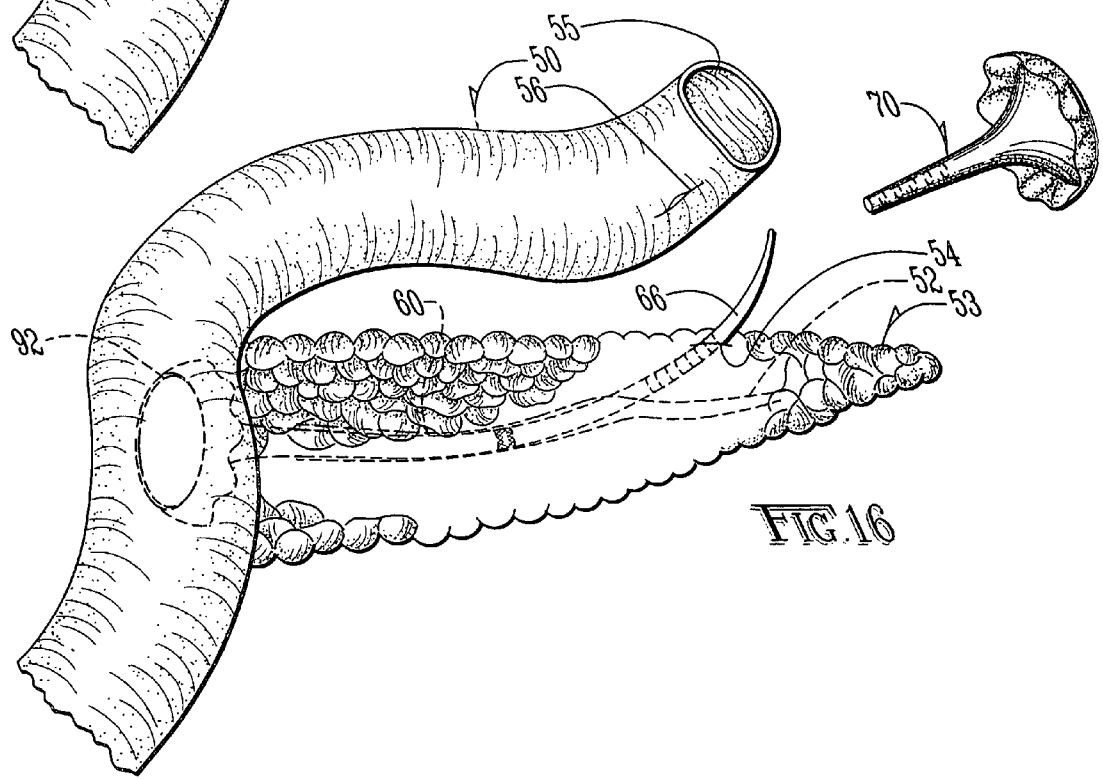

As shown in FIG. 16, the guide section 66 is then passed through a second incision 56 in the Roux limb. The second catheter 70 is passed into the open end 55 of the Roux limb 50 via the Seldinger Technique until the second end 75 of the second catheter 70 passes over the second section 68 of the first catheter 60. The Seldinger Technique is a method of introducing a catheter into a hollow lumen or cavity. A hollow needle is used to enter the lumen. A guidewire is passed through the needle and the needle is withdrawn. The catheter is then advanced over the guidewire. In this case, the guide section 66 acts as the guidewire in the Seldinger Technique. Note that in this embodiment, the means for connecting the catheters 60, 70 must be disposed on the exterior of the first catheter 60 and on the interior of the second catheter 70.

Figure 17:
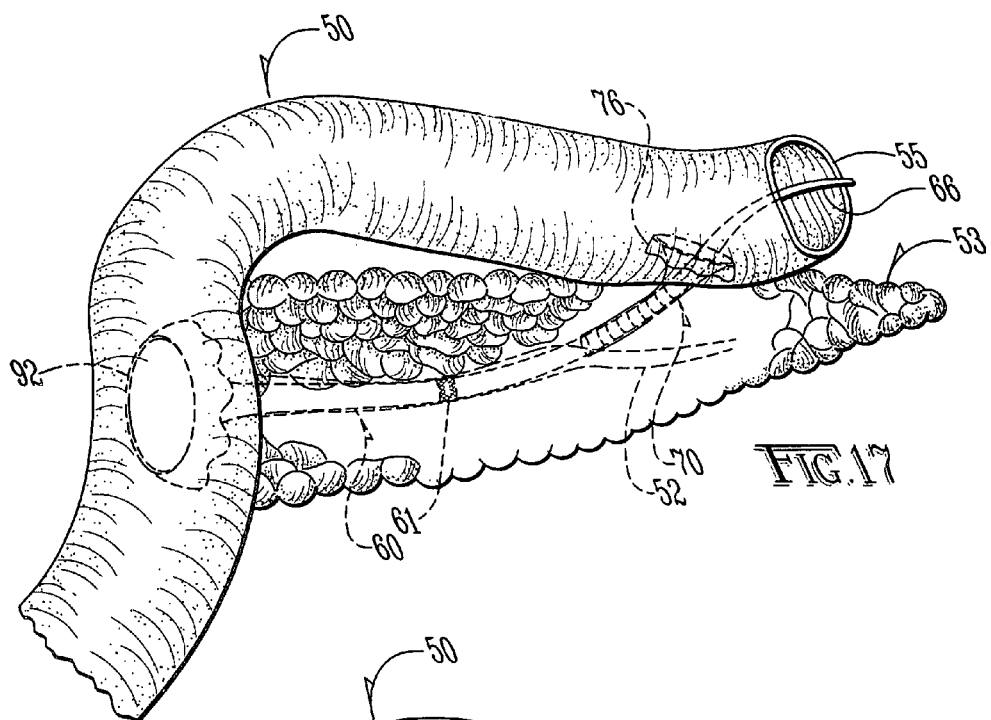
Figure 18:
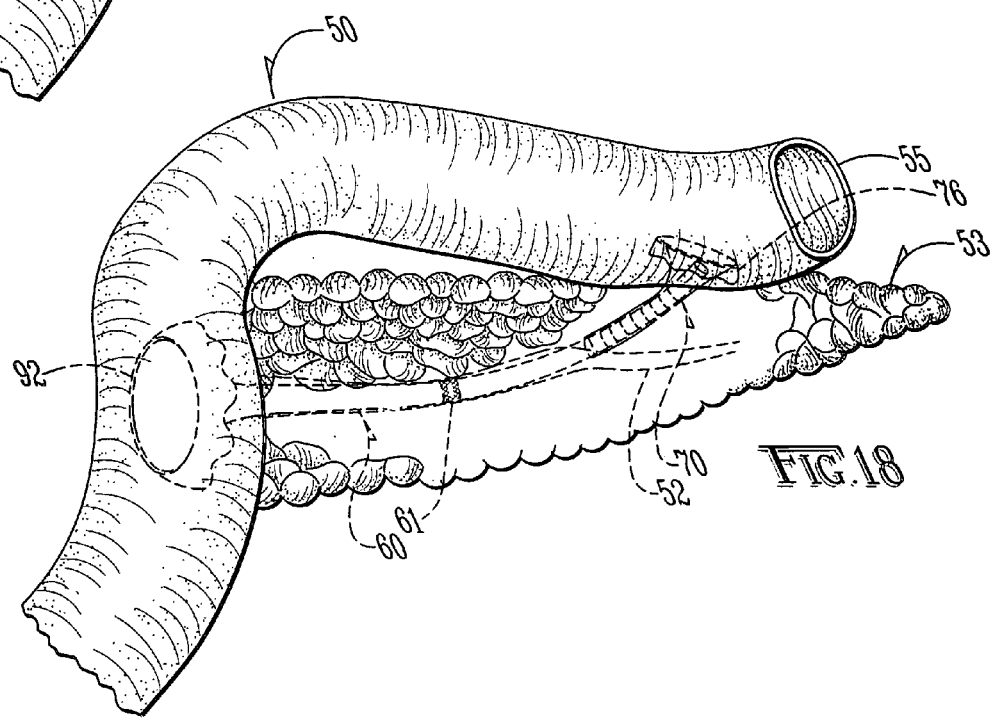

As shown in FIG. 17, the guide section 66 of the first catheter 60 protruding beyond the flange 76 of the second catheter 70 is trimmed off and the catheters 60, 70 are squeezed together for a snug fit. As shown in FIG. 18, the flange 92 of the first catheter 60 and the flange 76 of the second catheter 70 form two anastomoses—between the mucosa at the first enterotomy 51 and the pancreatic duct 52 and the other between the mucosa of the second enterotomy 56 and the exit opening 54 from the parenchyma. After sufficient time for the anastomoses to heal, the dissolvable mesh section 61 dissolves in 10-21 days and allows the joined catheters 60, 70 to separate into two pieces. Once the two pieces separate, they are extruded with normal bowel movements.

Figure 19:
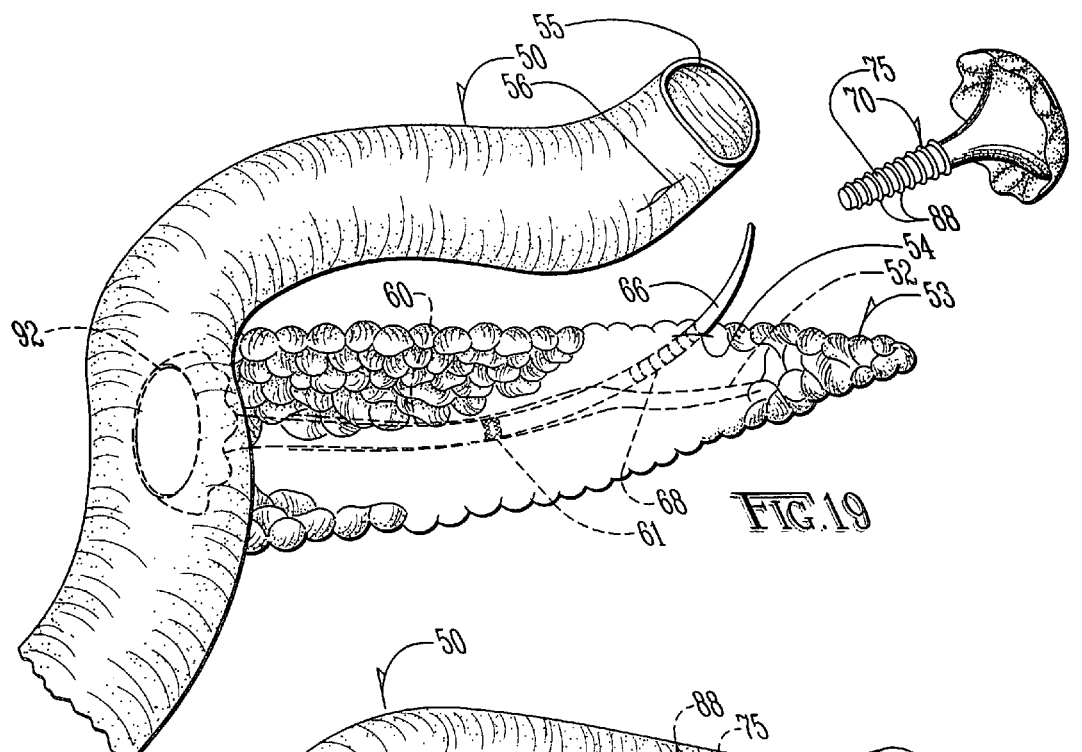
FIGS. 19 and 20 are perspective views showing the steps in one method of attachment of the catheters of the alternative embodiments of FIGS. 13A and 13B.
Figure 20:
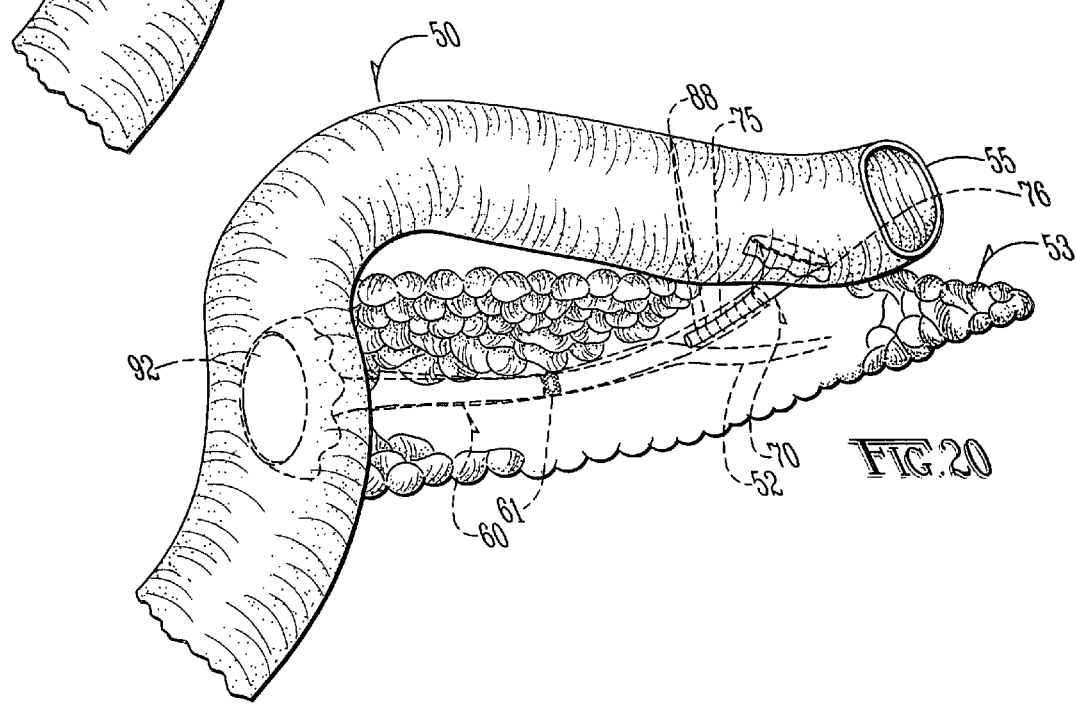

An alternative method of connecting the catheters 60, 70 is described with reference to FIGS. 19 and 20, where the means for connecting the catheters 60, 70 is disposed on the interior of first catheter 60 and on the exterior of second catheter 70. Rather than using the Seldinger Technique, after the first catheter is inserted into the pancreatic duct 52 and out through the parenchyma of the pancreas 53. The guide section 66 and any protruding portion of the second section 68 is trimmed flush with the surface of the pancreas 53. The second catheter 70 is placed into the open end 55 of the Roux limb 50 and then through the second enterotomy 56. The second end 75 of the second catheter 70 passes into the second section 68 of the first catheter 60 and snugged for a secure fit.

The features of the present invention may be used with other devices, such as gastrostomy and jejunostomy tubes. The process of the present invention may also be applied to laparoscopic procedures, thus facilitating conversion of difficult open pancreatic procedures to more facile minimally invasive procedures. It is intended that the present invention may be applied to all intestinal anastomoses in both open and closed procedures.

The present invention has been described with reference to certain preferred and alternative embodiments that are intended to be exemplary only and not limiting to the full scope of the present invention as set forth in the appended claims.

What is claimed is:

1. A catheterization system, comprising:
    a first catheter having a hollow interior communicating with a first opening at a first end and a second opening at a second end, said first end having a flange disposed at said first opening;
    a second catheter having a hollow interior communicating with a first opening at a first end and a second opening at a second end, said first end having a flange disposed at said first opening;
    means for connecting said first catheter to said second catheter at respective second ends to form a connected dual catheter; and
    dissolvable means for separating said connected dual catheter into a first nondissolvable portion comprising said flange of said first catheter and a second nondissolvable portion comprising said flange of said second catheter.

2. The system of claim 1, further comprising a guide member associated with said first catheter.

3. The system of claim 2, wherein said dissolvable means comprises a dissolvable section of one of said first catheter and said second catheter.

4. The system of claim 2, wherein said dissolvable means comprises a dissolvable suture, means for attaching said dissolvable suture to said first catheter, and means for attaching said dissolvable suture to said second catheter.

5. The system of claim 3 wherein said guide member comprises a guidewire integral to said second end of said first catheter, said guidewire having a penetrating tip.

6. The system of claim 4 wherein said guide member comprises a guidewire having a first end comprising means for attaching a suture and a second end comprising a penetrating tip.

7. The system of claim 4 wherein said means for attaching said dissolvable suture to said first catheter comprises a metal ring disposed at said first opening and a gap for passing a suture around said metal ring, and wherein said means for attaching said dissolvable suture to said second catheter comprises a metal ring disposed at said first opening and a gap for passing a suture around said metal ring.

8. The system of claim 3 wherein said dissolvable section comprises a dissolvable mesh.

9. The system of claim 3, wherein said first catheter comprises means disposed on said second end for threadedly engaging said second end of said second catheter and wherein said second catheter comprises means disposed on said second end for threadedly engaging said second end of said first catheter.

10. The system of claim 3, wherein said first catheter comprises means disposed on said second end for frictionally engaging said second end of said second catheter and wherein said second catheter comprises means disposed on said second end for frictionally engaging said second end of said first catheter.

11. The system of claim 3, wherein said first catheter comprises a plurality of ribs disposed on said second end, and said second catheter comprises a plurality of complementary recesses disposed on said second end for elastically engaging said plurality of ribs.

12. The system of claim 3, wherein said first catheter comprises a plurality of protuberances disposed on said second end, and said second catheter comprises a plurality of complementary holes disposed on said second end for elastically engaging said plurality of protuberances.

13. The system of claim 1, wherein said first catheter and said second catheter comprise fenestrations communicating with respective said hollow interiors.

14. The system of claim 1, wherein said first end of said first catheter comprises a flared portion terminating in said first opening and said first end of said second catheter comprises a flared portion terminating in said first opening, means for compressing said flared portion and narrowing said flange, comprising a member having a bore characterized by a diameter smaller than a diameter of said flared portion.

* * * * *